(12) United States Patent
Damiano, Jr. et al.

(10) Patent No.: US 8,920,723 B2
(45) Date of Patent: Dec. 30, 2014

(54) SAMPLE SUPPORT STRUCTURE AND METHODS

(75) Inventors: John Damiano, Jr., Apex, NC (US); Stephen E. Mick, Apex, NC (US); David P. Nackashi, Raleigh, NC (US)

(73) Assignee: Protochips, Inc., Raleigh, NC (US)

( * ) Notice: Subject to any disclaimer, the term of this patent is extended or adjusted under 35 U.S.C. 154(b) by 989 days.

(21) Appl. No.: 12/515,131

(22) PCT Filed: Nov. 16, 2007

(86) PCT No.: PCT/US2007/084945
§ 371 (c)(1),
(2), (4) Date: Feb. 17, 2010

(87) PCT Pub. No.: WO2008/061224
PCT Pub. Date: May 22, 2008

(65) Prior Publication Data
US 2010/0143198 A1    Jun. 10, 2010

Related U.S. Application Data

(60) Provisional application No. 60/866,085, filed on Nov. 16, 2006.

(51) Int. Cl.
*G01N 15/06*     (2006.01)
(Continued)

(52) U.S. Cl.
CPC .......... *G01N 23/046* (2013.01); *G01N 27/4167* (2013.01); *B82Y 10/00* (2013.01);
(Continued)

(58) Field of Classification Search
CPC ............ G01N 27/302; G01N 27/3335; G01N 27/4167; G01N 27/06; B82Y 40/00; B82Y 30/00; B82Y 10/00
USPC ............ 422/68.1, 82.05, 82.06, 82.08, 82.09, 422/82.11, 99, 407; 435/164, 165, 283.1, 435/287.1, 287.2, 4, 5, 7.2, 7.9; 436/149, 436/164, 172, 174, 518, 805, 809; 356/369; 506/9
See application file for complete search history.

(56) References Cited

U.S. PATENT DOCUMENTS 4,543,266 A * 9/1985 Matsuo et al. .................. 216/12
5,334,837 A    8/1994 Ikeda et al.
(Continued)

FOREIGN PATENT DOCUMENTS

| JP | 57145260 A | 9/1982 |
|----|-----------|--------|
| WO | WO 2005007276 A1 * | 1/2005 |
| WO | 2006031104 A1 | 3/2006 |

OTHER PUBLICATIONS

Tong et al, "Silicon Nitride Nanosieve Membrane" Nanoletters, vol. 4, No. 2, Jan. 13, 2004, pp. 283-287.*

(Continued)

*Primary Examiner* — Dennis M White
(74) *Attorney, Agent, or Firm* — Tristan A. Fuierer; Moore & Van Allen, PLLC (57) ABSTRACT

A sample support structure comprising a sample support manufactured from a semiconductor material and having one or more openings therein. Methods of making and using the sample support structure.

20 Claims, 6 Drawing Sheets

(51) Int. Cl.
*G01N 23/04* (2006.01)
*H01J 37/20* (2006.01)
*G01N 27/416* (2006.01)
*B82Y 10/00* (2011.01)
*B82Y 30/00* (2011.01)
*G01N 27/30* (2006.01)
*G01N 27/06* (2006.01)
*G01N 27/333* (2006.01)
*B82Y 40/00* (2011.01)

(52) U.S. Cl.
CPC .............. *B82Y 30/00* (2013.01); *G01N 27/302* (2013.01); *G01N 27/06* (2013.01); *G01N 27/3335* (2013.01); *B82Y 40/00* (2013.01); *H01J 37/20* (2013.01); *H01J 2237/26* (2013.01); *H01J 2237/28* (2013.01); *Y10S 436/805* (2013.01); *Y10S 436/809* (2013.01)
USPC ................... 422/68.1; 422/82.05; 422/82.06; 422/82.08; 422/82.09; 422/82.11; 422/407; 435/164; 435/165; 435/283.1; 435/287.1; 435/287.2; 435/4; 435/5; 435/7.2; 435/7.9; 436/149; 436/164; 436/172; 436/174; 436/518; 436/805; 436/809; 356/369; 506/9

(56) References Cited

U.S. PATENT DOCUMENTS

| | | | |
|---|---|---|---|
| 5,376,241 A * | 12/1994 | Shor et al. ..................... | 205/645 |
| 6,140,652 A | 10/2000 | Shlepr et al. | |
| 6,287,517 B1 | 9/2001 | Ackley et al. | |
| 6,841,788 B1 | 1/2005 | Robinson et al. | |
| 7,283,228 B2 | 10/2007 | Zhang et al. | |
| 2007/0039471 A1 * | 2/2007 | Hofmann ........................... | 96/4 |

OTHER PUBLICATIONS

Tong et al, "A Hydrogen Separation Module Based on Wafer-Scale Micromachined Palladium-Silver Alloy Membranes" 12th International Converence on Solid State Sensors, Actuators and Microsystems, Boston, Jun. 8-12,2003, pp. 1742-1745.*
Shi et al, "Modifying residual stress and stress gradient in LPCVD Si3N4 film with ion implantation" Sensors and Actuators A 130-131, available online Nov. 21, 2005, pp. 352-357.*
DuraSiN(TM), Internet Archive capture on May 7, 2005 from www.emsdiasum.com/microscopy/products/grids/durasin.aspx, pp. 1-7.*
International Search Authority, International Search Report and Written Opinion, PCT/US2007/084945, Mar. 17, 2008.
International Bureau, International Preliminary Report on Patentability, PCT/US2007/084945, May 19, 2009.
Supplementary European Search Report, Jul. 27, 2012.

* cited by examiner

SAMPLE SUPPORT STRUCTURE AND METHODS

CROSS-REFERENCE TO RELATED APPLICATIONS

This application is filed under the provisions of 35 U.S.C. §371 and claims the priority of International Patent Application No. PCT/US07/84945 filed on 16 Nov. 2007 entitled "Sample Support Structure and Methods" in the name of John Damiano Jr., et al., which claims priority of U.S. Provisional Patent Application No. 60/866,085 filed on 16 Nov. 2006, both of which are hereby incorporated by reference herein in their entirety.

FIELD OF THE INVENTION

The invention relates to sample support structures, methods of making sample support structures, and methods of using sample support structures. The sample support structures may be useful in electron microscopy. The sample support structures have desired properties, such as: minimal drift during analysis by electron microscopy; increased rigidity; and conductivity of the sample support structures, including at low temperatures; and decreased electron charging.

BACKGROUND OF THE INVENTION

During electron microscopy or ion-beam analysis, a test sample is placed on a sample support. Typically, the sample supports consist of a metal grid, often copper, gold, nickel, or molybdenum. For certain types of analysis, a thin carbon film is typically placed atop the metal grid. The carbon film is very thin, conductive, and often contains holes. When used during cryo-electron microscopy, this holey carbon film allows for analysis of very small specimens or specimens embedded in vitreous ice.

There are several problems with the existing sample support technology. During analysis, the very thin carbon film tends to move or drift due to its lack of thermal and mechanical stability, which degrades the ability to achieve highest resolution images. The holey carbon film is supported by a metal grid, however, the presence of grid bars blocks imaging area and limits the ability to perform tomographic analysis. Thermal instability exists due to coefficient of thermal expansion (CTE) mismatch between the metal grid and the carbon film which may create wrinkles on or tear the carbon film. In addition, since the conductivity of the carbon degrades quickly at very low temperatures, deflection during imaging results due to electron-beam induced charging.

Accordingly, there exists a need in the art for sample supports with improved properties including, but not limited to, minimal drift during analysis by electron microscopy; increased rigidity; and conductivity of the sample support structures, including at low temperatures; and decreased electron charging. The present invention addresses this need.

SUMMARY OF THE INVENTION

A first aspect of the present invention relates to a sample support structure. The sample support structure contains a sample support manufactured from a semiconductor material and having one or more holes. The semiconductor material may include amorphous silicon, polycrystalline silicon, monocrystalline silicon, silicon nitride, silicon carbide, boron nitride, aluminum nitride, graphite, graphene, other semiconductor materials or ceramics, and combinations thereof. The sample support may contain an array, or multiple arrays, of holes which may be substantially centrally located on the sample support.

In the sample support structure of the present invention, the sample support may have a thickness that is less than about 500000 Angstroms and a Young's modulus of greater than 300 GPa. The sample support may have a diameter which ranges from about 1 to about 20 mm, about 2 to about 8 mm, or about 3 mm. The sample support may have a thickness which ranges from about 1 to about 500000 Angstroms, about 100 to about 5000 Angstroms, or 200 to about 1000 Angstroms. The holes in the sample support may have a diameter ranging from about 0.05 to about 100 µm, about 0.5 to about 4 µm, or about 1 to about 3 µm.

In a further aspect of the invention, the sample support structure may include an underlying base. The base may include monocrystalline silicon, polycrystalline silicon, amorphous silicon, alumina, quartz, fused silica, boron nitride, silicon carbide, other semiconductor materials, metals, ceramics, conducting oxides, or combinations thereof. In one aspect, the base may have a shape which substantially tracks the perimeter of the sample support; the base may contain an opening, the perimeter of which substantially tracks a perimeter of the one or more holes in the sample support; or both. The base may contain a single opening, or multiple openings that may be aligned with the array or multiple arrays of holes in the sample support. The sample support may contain an array of holes therein, and the base may contain a single opening substantially surrounding the array of holes. The structure may contain a perimeter region, surrounding the array of holes, which may lack holes. The shape of the sample support structure may be generally circular.

In the sample support structure of the present invention, the base may have a thickness which ranges from about 2 to about 750 µm, about 4 to about 150 µm, or about 5 to about 50 µm.

An aspect of the present invention relates to a method of making a sample support structure. The method may comprise the steps of: (a) providing a substrate comprising three layers: (i) a top base layer containing an etchable semiconductor material; (ii) a middle insulator layer containing an etchable semiconductor material; and (iii) a bottom substrate layer containing an etchable semiconductor material; wherein the base layer is etchable without substantial etching of the insulator layer, and the insulator layer is etchable without substantial etching of the base layer; (b) applying a sample support layer to the top base layer wherein the sample support layer comprises an etchable semiconductor material; (c) patterning dimensions of a sample support onto the sample support layer, including one or more holes; (d) etching the sample support layer to achieve dimensions established by the patterning step, including the one or more holes; (e) etching the base layer to achieve dimensions of a base; (f) etching the insulator layer to release or substantially release the insulator layer, thereby freeing or substantially freeing a sample support structure containing: (i) a sample support containing one or more holes therein; and (ii) a base underlying the sample support containing an opening therein substantially surrounding the one or more holes of the sample support.

In the method of making a sample support structure, the sample support layer may include silicon carbide, silicon nitride, aluminum nitride, boron nitride, monocrystalline silicon, polycrystalline silicon, amorphous silicon, other semiconductor materials or ceramics, and combinations thereof. The base layer may include monocrystalline silicon, polycrystalline silicon, amorphous silicon, alumina, quartz, fused silica, boron nitride, silicon carbide, other semiconductor materials, metals, ceramics, conducting oxide, and combinations thereof. The bottom substrate layer may include monocrystalline silicon, polycrystalline silicon, amorphous silicon, alumina, quartz, fused silica, boron nitride, silicon carbide, other semiconductor materials, metals, ceramics, conducting oxide, and combinations thereof. The insulator layer may contain silicon dioxide, fused silica, quartz, aluminum nitride, conducting oxides, silicon monoxide, and combinations thereof.

In an aspect of the above method, step (d) may include etching the sample support layer using wet chemical etching, reactive ion etching (RIE), deep reactive ion etching (DRIE), or ion milling. Step (c) may include patterning a shape and diameter on the sample support layer; or patterning an array, or multiple arrays, of holes in a center portion of the sample support layer. Step (e) may include etching the base layer through to the insulator layer to leave an opening in the base layer generally circumscribing the array, or the multiple arrays, of holes. Step (e) may include etching the base layer around the sample support to yield a base layer having an outer perimeter that is substantially the same shape as the sample support. Step (b) may include applying the sample support layer using a technique selected from low-pressure chemical vapor deposition (LPCVD), physical vapor deposition (PVD), plasma-enhanced chemical vapor deposition (PECVD), and metal-organic chemical vapor deposition (MOCVD).

In another aspect of the above-described method of the present invention, the holes may be two or more holes each having a diameter of about 1 to about 3 µm, or about 3 to about 5 µm. The two or more holes may have a diameter of about 2 µm, and a pitch of about 4 µm. The array of patterned holes may be approximately circular, and may have a diameter ranging from about 0.1 to about 0.9, or about 0.25 to about 2 mm of the diameter of the sample support. The sample support may include a perimeter region lacking holes which may have a width of about 0.25 to about 2 mm. The sample support layer may be etched using an $SF_6$ based etch recipe. The base layer may be etched using a deep reactive ion etching technique. Step (e) of the above method may include (a) a first step comprising deep reactive ion etching; and (b) a second step comprising solution comprising hydrofluoric acid, nitric acid, and acetic acid (HNA). The insulator layer may be etched with concentrated hydrofluoric acid. The above method may further include applying a sample support layer to the bottom of the substrate.

A further aspect of the invention relates to methods of using the sample support structures of the present invention. Included is a method of analyzing a sample comprising placing the sample on the sample support structure of the present invention and analyzing the sample using an electron microscopy technique. In a further aspect, the sample may include a biological specimen. The sample may include a protein, a peptide, or a portion thereof. The sample may further include a compound that interacts with the protein, peptide, or portion thereof. The sample may include a chemical compound. The analysis may occur at temperatures ranging from about –270 to about 0° C.

BRIEF DESCRIPTION OF THE DRAWINGS

FIG. 3 illustrates the sample support layer 20 on the frontside of the substrate patterned using photolithography followed by reactive ion etching or wet chemical etching. In FIGS. 3A and 3B, a sample support structure containing an array of holes is illustrated. In FIGS. 3C and 3D, a sample support structure containing multiple arrays of holes is illustrated.

In FIGS. 4A and 4B, a sample support structure containing an array of holes is illustrated. In FIGS. 4C and 4D, a sample support structure containing multiple arrays of holes is illustrated.

In FIGS. 5A and 5B, a sample support structure containing an array of holes is illustrated. In FIGS. 5C and 5D, a sample support structure containing multiple arrays of holes is illustrated.

FIG. 6 illustrates the support structure 60, comprised of frame region 41 and sample support membrane area 40, released from the substrate layer 103.

DETAILED DESCRIPTION OF THE INVENTION

The present invention relates to sample support structures, methods of making sample support structures, and methods of using sample support structures. The sample support structures are useful for supporting samples for analysis using microscopic techniques, such as electron microscopy techniques. The sample support structures have a variety of desirable properties, such as one or more of the following: minimal drift during analysis by electron microscopy compared to amorphous carbon films; increased rigidity of the sample support layer, with Young's Modulus 3 to 9 times larger than amorphous carbon; increased conductivity of sample support layer, even at low temperatures; and improved CTE matching between sample support film and base layer compared to conventional carbon film on metal grid. The sample support structures of the present invention are useful in a variety of electron microscopy techniques, such as transmission electron microscopy and related techniques.

As defined herein, "semiconductor" means a material, such as silicon, that is intermediate in electrical conductivity between conductors and insulators.

As defined herein, "photolithography" means a process, which uses beams of light, projected through a reticle, to pattern or etch a photosensitive material.

As defined herein, "low-pressure chemical vapor deposition (LPCVD)" means a technique in which one or more gaseous reactors are used to form a solid insulating or conducting layer on the surface of a substrate under low pressure and high temperature conditions.

As defined herein, an "opening" corresponds to a region generally circumscribed by base layer material that was not etchingly removed, i.e., the base. Put another way, the opening(s) in the base layer generally take the shape of the general pattern of the at least one array of holes and the base generally takes the shape of the outer perimeter of the sample support that lacks holes. Put still another way, the opening(s) are circumscribed by the base and include the sample support membrane as the ceiling when the base is in contact with a horizontal surface.

As defined herein, "without substantial etching" is defined the etching removal of less than about 5 wt. % of the material, preferably less than about 2 wt. %, even more preferably less than 1 wt. %, based on the total weight of the material.

As defined herein, "pitch" is defined as the minimum distance from the center of a given feature to the center of an adjacent feature. For example, a non-limiting example is pitch corresponds to the minimum distance from the center of one hole to the center of another hold.

The invention provides a sample support structure. The sample support structure may generally include sample support and a base.

The sample support serves to support a sample during analysis. The sample support is preferably rigid to decrease instability during sample analysis as well as conductive to reduce charge buildup which can interfere with sample analysis. The stress in the sample support is low and tensile. The sample support may include a sample support layer. In an embodiment, the sample support includes holes and/or arrays of holes.

In a non-limiting embodiment, the sample support may be a sample support layer. For illustrative, non-limiting, purposes, sample support layers are referenced herein as examples of sample supports; however, the descriptions are intended to be non-limiting. Other sample supports which are not considered to be layers are known to one of skill in the art and are contemplated herein.

The Young's modulus of the sample support is a measure of its rigidity. In one embodiment, the sample support may have a Young's modulus of greater than about 150 GPa. In a further embodiment, the sample support may have a Young's modulus of greater than about 300 GPa. In a further embodiment, the sample support may have a Young's modulus of greater than about 400 GPa. In a still further embodiment, the Young's modulus may be approximately 450 GPa.

In an embodiment, the sample support layer has tensile stress. In one aspect of this embodiment, the tensile stress is greater than 0 MPa. In a further aspect, the tensile stress is from about 100 to about 400 MPa. In a further aspect of this embodiment, the tensile stress is from about 200 to about 300 MPa.

In an embodiment, the sample support layers are thicker, can be doped, and are less resistive than reference supports. In an embodiment, the resistivity is less than about 10 ohm-cm. In a further embodiment, the resistivity is from about 0.01 to about 5 ohm-cm. In a further embodiment, the resistivity is approximately 0.025 ohm-cm.

The dimensions, such as thickness, shape, diameter, holes, and/or arrays of holes of the sample support may vary depending on the intended use of the sample support structure. For example, the thickness of the sample support may suitably range from about 1 (single monolayer) to about 500000 Angstroms, or from about 100 to about 5000 Angstroms, or from about 200 to about 1000 Angstroms. Any shape which does not eliminate the sample support structure from performing its intended use is suitable. Examples of suitable shapes include circular shapes, ovular shapes, and polygonal shapes. The sample support may typically have a diameter ranging from less than about 1 mm to about 20 mm, or from about 2 mm to about 8 mm, or may be about 3 mm (such as 3.05 mm). Larger or smaller structures are possible within the scope of the invention.

A wide variety of materials may be used for the sample support. Preferred materials are semiconductor materials, such as monocrystalline silicon, polycrystalline silicon, amorphous silicon, silicon carbide, silicon nitride, aluminum nitride, boron nitride, gallium nitride, graphene, graphite, other semiconductor materials, conductive oxides and ceramics, as well as other materials known to one of skill in the art, and combinations thereof. Semiconductor materials may be doped to improve conductivity. Examples of suitable doped semiconductor materials for use in the sample support layer include, but are not limited to: silicon carbide with nitrogen doping to achieve resistivity 0.025 ohm-cm; and amorphous silicon or monocrystalline silicon or polycrystalline silicon with boron doping to achieve resistivity 0.025 ohm-cm.

The sample support may include one or more holes. Multiple holes may be arranged as one or more arrays of holes. The holes may be any shape which is suitable for the intended use of the holes, such as circular shapes, substantially circular shapes, ovular shapes, substantially ovular shapes, polygonal shapes and/or substantially polygonal shapes. Further, the array or arrays may be arranged in any of a wide variety of patterns, such as circular patterns, substantially circular patterns, ovular patterns, substantially ovular patterns, polygonal patterns, and/or substantially polygonal patterns.

The one or more holes and/or arrays of holes may be positioned anywhere on the sample support. For example, the one or more holes and/or arrays of holes may be generally centrally positioned on the sample support. Further, in some embodiments holes and/or arrays of holes are concentrated in one or more regions of the sample support leaving one or more other regions without holes. The number of holes in a sample support may also vary. For example, the invention may include a sample support with about 1 to about $1\times10^{10}$ holes, about $1\times10^{2}$ to about $1\times10^{7}$ holes, or about $1\times10^{4}$ to about $1\times10^{6}$ holes.

The size of the holes may vary according to the use of the sample support structure. For example, the diameter holes may vary from about 0.05 to about 100 μm, or from about 0.05 to about 5 μm, or from about 0.5 to about 4 μm, or about 1 to about 3 μm, or may be about 2 μm.

In arrays, the pitch of the holes may vary according to the use of the sample support structure. For example, the pitch may vary from about 0.10 μm to about 6 μm, or about 3 μm to about 5 μm, or about 3.5 to about 4.5 μm, or the pitch may be about 4 μm.

For example, in one embodiment, a group or array of holes is concentrated in a central region of the sample support leaving a perimeter region which is lacking in holes. The diameter of the central holey region may vary depending on the desired use of the sample support structure. For example, the patterned array of holes may have a diameter ranging from about 0.1 to about 0.9, or from about 0.2 to about 0.8, or from about 0.3 to about 0.7 of the diameter of the sample support. For example, the patterned array of holes may have a diameter of about 0.25 to about 2.5 mm, or about 0.5 to about 2 mm, or about 0.75 to about 1.5 mm, or about 1 mm. The width of the perimeter region lacking holes may vary depending on the desired use of the sample support structure. For example, the width may be from about 0.25 nm to about 2.5 mm, or about 0.5 to about 2 mm, or about 0.75 to about 1.5 mm, or about 1 mm.

In a particular non-limiting embodiment, the sample support layer may have a diameter of about 3 mm, a central region with a patterned array of holes may have a diameter of about 1 mm, and an outer perimeter lacking holes may have a width of about 1 mm.

In another embodiment, the sample support may contain multiple arrays of holes. For example, the multiple arrays may be positioned such that regions of the sample support may contain holes, and regions of the sample support may not contain holes. The sizes, and positioning, of the multiple arrays of holes may vary. In an aspect of this embodiment, the regions of the sample support that do not contain holes is large enough that the base layer underneath the region is not fully undercut during the base layer etch. In a further aspect of this embodiment, regions of the sample support that do not contain holes may span the entire length and/or width of the sample support. Further, regions of the base layer underneath these regions of the sample support may span the entire length and/or width of the sample support. The sample supports of this embodiment may be even stronger than the sample supports of other embodiments.

In a particular non-limiting embodiment, the sample support layer may have a diameter of about 3 mm, a central region may have a diameter of about 1 mm, the central region may have regions containing multiple arrays of holes as well as regions which do not contain holes, and an outer perimeter lacking holes may have a width of about 1 mm.

The sample support structure may include a base. In general, the function of the base is to provide a thickened support which stabilizes the sample support structure. In one embodiment, the base has a shape which generally corresponds to the shape of the sample support. The base may include a base layer.

In a non-limiting embodiment, the base may be a base layer. For illustrative, non-limiting, purposes, base layers are referenced herein as examples of bases; however, the descriptions are intended to be non-limiting. Other bases which are not considered to be layers are known to one of skill in the art and are contemplated herein.

A wide variety of materials may be used for the base. Examples of suitable materials for the base of the sample support structure include monocrystalline silicon, polycrystalline silicon, amorphous silicon, alumina, quartz, fused silica, boron nitride, silicon carbide, other semiconductor materials, metals, ceramics, conducting oxides, and combinations thereof. The thickness of the base may vary depending on the desired use of the sample support structure. For example, the base may have a thickness which ranges from about 2 to about 750 μm, from about 4 to about 150 μm, or from about 5 to about 50 μm.

As described above, in one embodiment, the sample support has holes. In an aspect of this embodiment, the base contains one or more openings. The holes of the sample support may be visible through the opening or openings of the base. Where the base contains openings, the openings may be generally in alignment with the holes of the sample support. Where the base contains a single opening, the opening may be the size of the entire center portion of the sample support, as described above. Where the base contains multiple openings, the multiple openings may align with the multiple arrays of holes in the sample support, as described above, and the one or more of the multiple openings in the base may be the same size as one or more of the multiple arrays of holes in the sample support. Further, as described above, in an aspect of this embodiment, the regions of the sample support that do not contain holes is large enough that the base layer underneath the region is not fully undercut during the base layer etch. Further, regions of the base layer underneath these regions of the sample support may span the entire length and/or width of the sample support. The sample support structures of this embodiment may be even stronger than the sample support structures of other embodiments.

In an additional embodiment, the sample support structure may include additional layers. For example, the sample support structure may include an insulator layer and/or a semiconductor substrate layer.

The sample support of the sample support structure may be joined to the base of the sample support structure using a variety of joining mechanisms, as described in more detail herein.

An embodiment of the present invention relates to methods of making a sample support structure. In an aspect of the embodiment, the method may comprise one or more of the following steps:

providing a semiconductor substrate 10;
applying a sample support layer 20 to the semiconductor substrate 10;
patterning the dimensions of the sample support onto the sample support layer 20;
etching the sample support layer 20 to achieve the patterned dimensions;
etching the base layer 101 of the semiconductor substrate 10 to create the base; and/or
etching the insulator layer of the semiconductor substrate to release the sample support structure.

Additionally, the support structure may include features that strengthen the specimen support during the manufacturing process but that can be removed during (or after the processing) so as not to limit the functionality or utility of the specimen support.

The substrate may include a base layer 101. Base layer 101 serves as the material for forming the base of the sample support structure. As such, it should have a thickness that is proportional to the desired thickness of the base. In a preferred embodiment, the thickness of base layer 101 ranges from about 2 to about 750 microns, or from about 4 to about 150 microns, or from about 5 to about 50 microns. A variety of alternative materials may be used for base layer 101. Examples include, but are not limited to, monocrystalline silicon, polycrystalline silicon, amorphous silicon, alumina, quartz, fused silica, boron nitride, silicon carbide, other semiconductor materials, metals, ceramics, conducting oxides, and combinations thereof.

The substrate may include a substrate layer 103. The substrate layer 103 serves to thicken the substrate during processing to facilitate handling of the material. Consequently, a wide range of thicknesses is acceptable, depending on specific handling requirements. In one embodiment, the substrate layer 103 has a thickness ranging from about 100 to about 525 microns. A variety of alternative materials may be used for silicon substrate 103. Examples include, but are not limited to, monocrystalline silicon, polycrystalline silicon, amorphous silicon, alumina, quartz, fused silica, boron nitride, silicon carbide, other semiconductor materials, metals, ceramics, conducting oxide, and combinations thereof.

The substrate may include an insulator layer 105. The insulator layer 105 serves to stop etching of the base layer 101 during processing, thereby establishing the dimensions of the base of the sample support structure. Any thickness which serves this purpose will be sufficient. In one embodiment, the insulator layer 105 has a thickness ranging from about 0.01 to about 50 microns. A variety of alternative materials may be used for insulator layer 105. Materials may, for example, be selected based on resistance to etching by the desired etchant for use in etching the base layer 101. Examples of suitable materials for use in insulator layer 105 include silicon dioxide, fused silica, quartz, aluminum nitride, conducting oxides, silicon monoxide, and combinations thereof.

Figure 1:
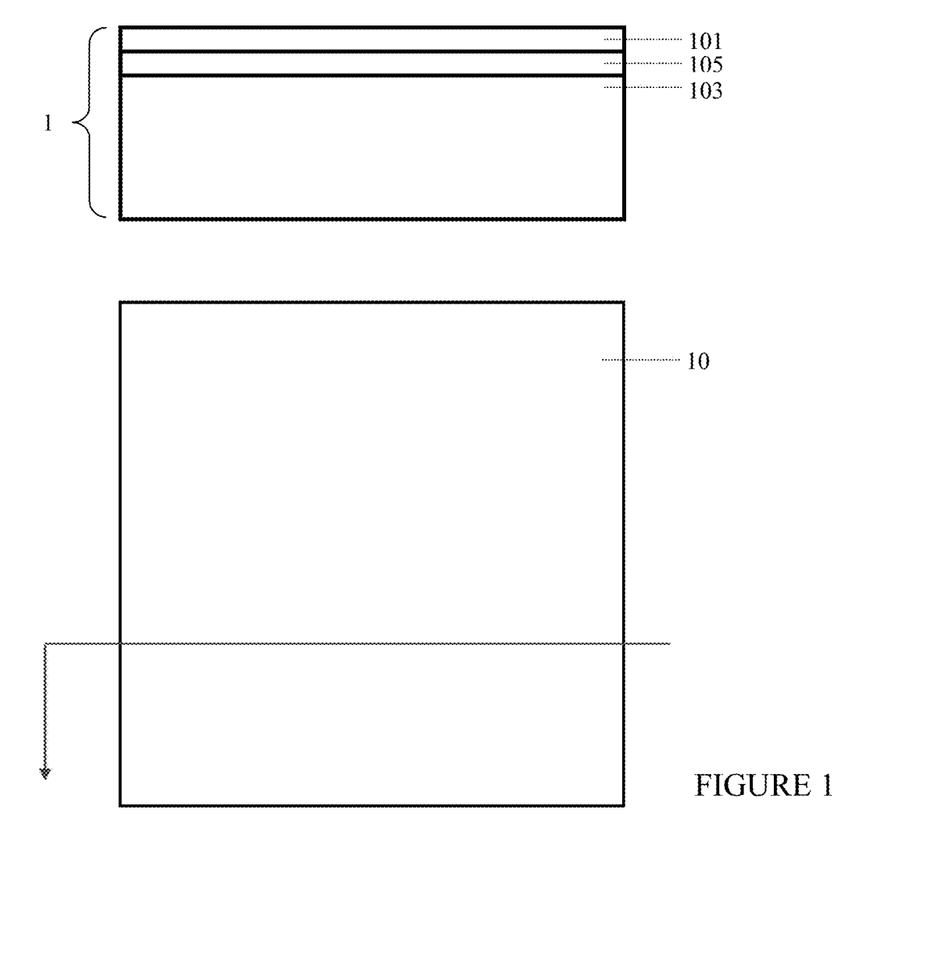
FIG. 1 illustrates a silicon-on-insulator semiconductor substrate.

FIG. 1 shows one embodiment of a substrate 10, e.g., a silicon-on-insulator. The substrate 10 includes base layer 101; substrate layer 103; and insulator layer 105. Other substrates contemplated include silicon, quartz, alumina, etc.

In one alternative embodiment, where a thick base is desirable, the insulator layer may be omitted, so that during processing, etching of a thick base layer under the sample support layer yields a platform with a thick base.

Figure 2:
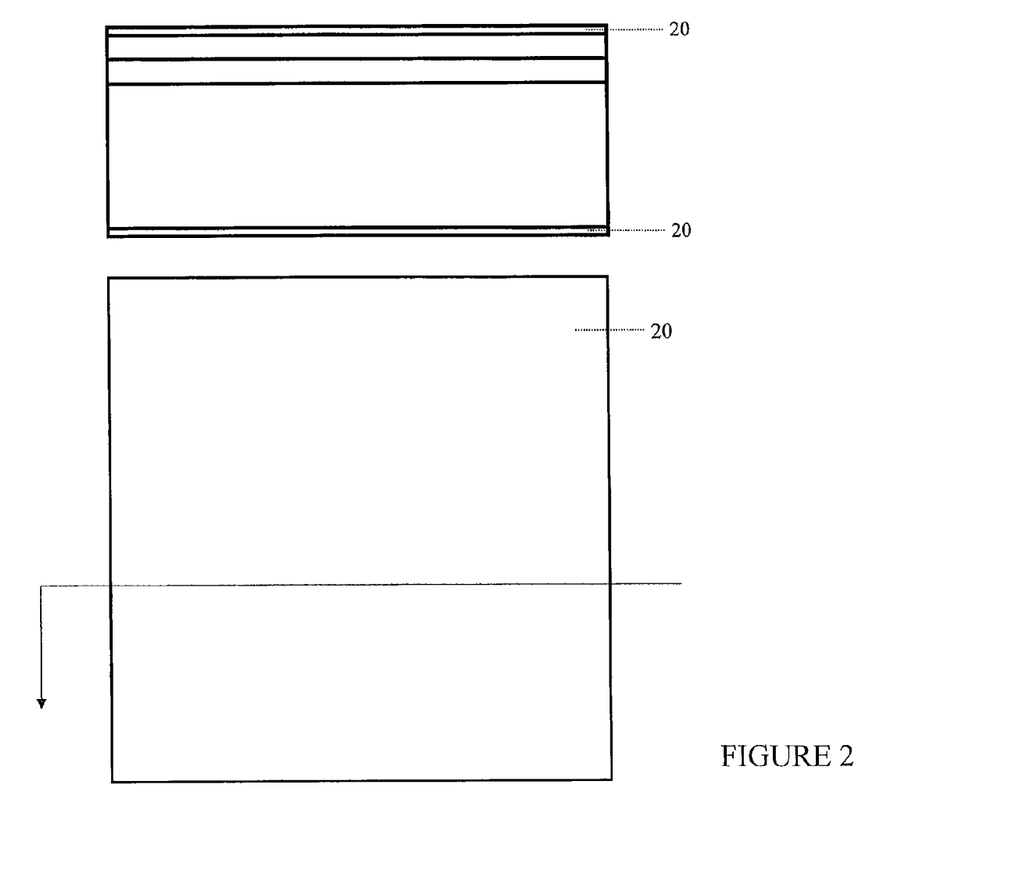
FIG. 2 shows a sample support layer 20 deposited on the frontside and backside surfaces of the substrate.

A sample support layer 20 is applied to the top layer of the substrate or applied to both the top and bottom layers of the substrate (as illustrated in FIG. 2). The purpose of the sample support layer is to provide a thin, rigid, conductive support for holding samples. A wide variety of materials may be used.

Various sample support dimensions and materials are described hereinabove, and the invention includes application of sample support layers utilizing such materials and/or suitable for attaining any of the dimensions indicated.

The sample support layer may be applied using a variety of deposition processes. For example, the sample support may be applied to the base using a chemical vapor deposition technique, such as low-pressure chemical vapor deposition (LPCVD), physical vapor deposition (PVD), plasma-enhanced chemical vapor deposition (PECVD), metal-organic chemical vapor deposition (MOCVD), atomic layer deposition (ALD), as well as electroplating/electrodeposition techniques, or any combination of these techniques. Examples of suitable chemical vapor deposition techniques are described in Hugh O. Pierson, *Handbook of Chemical Vapor Deposition, Second Edition: Principles, Technologies and Applications*, Noyes Publications; 2 edition (September 1999); and in Michael L. Hitchman, Chemical Vapor Deposition, Elsevier Limited; 1st edition (Jan. 1, 2001); the entire disclosure of which are incorporated herein by reference.

The dimensions of the sample support are patterned onto the sample support layer (see FIG. 3). For example, the patterning may include the establishment of the perimeter of the sample support layer 20 as well as one or more holes or one or more arrays of holes 30. Various dimensions of samples supports, holes, and arrays of holes are described hereinabove, and the invention will be understood to include the use of patterning techniques to prepare any of the dimensions indicated.

A variety of patterning techniques for patterning may be employed. In one embodiment, dimensions of the sample support are patterned using photolithography. A variety of suitable photolithography techniques are described in Harry J. Levinson, *Principles of Lithography*, SPIE-International Society for Optical Engine; 2nd ed. (February 2005), the entire disclosure of which is incorporated herein by reference.

The sample support layer may be etched to achieve the dimensions patterned thereon. Etching may be accomplished using a variety of etching techniques. The specific techniques selected will correspond to the material being used for the sample support layer. Examples of suitable techniques include wet etching, reactive ion etching, sputtering, ion milling, or a combination of these.

In one embodiment, the material used for the sample support layer is silicon carbide and the etching technique includes a technique suitable for etching silicon carbide. For example, the silicon carbide etch process may utilize an $SF_6$-based reactive ion etching recipe, with a flow rate of 40 sccm $SF_6$, 2000 W source power, and 110 W substrate power.

Figure 4:
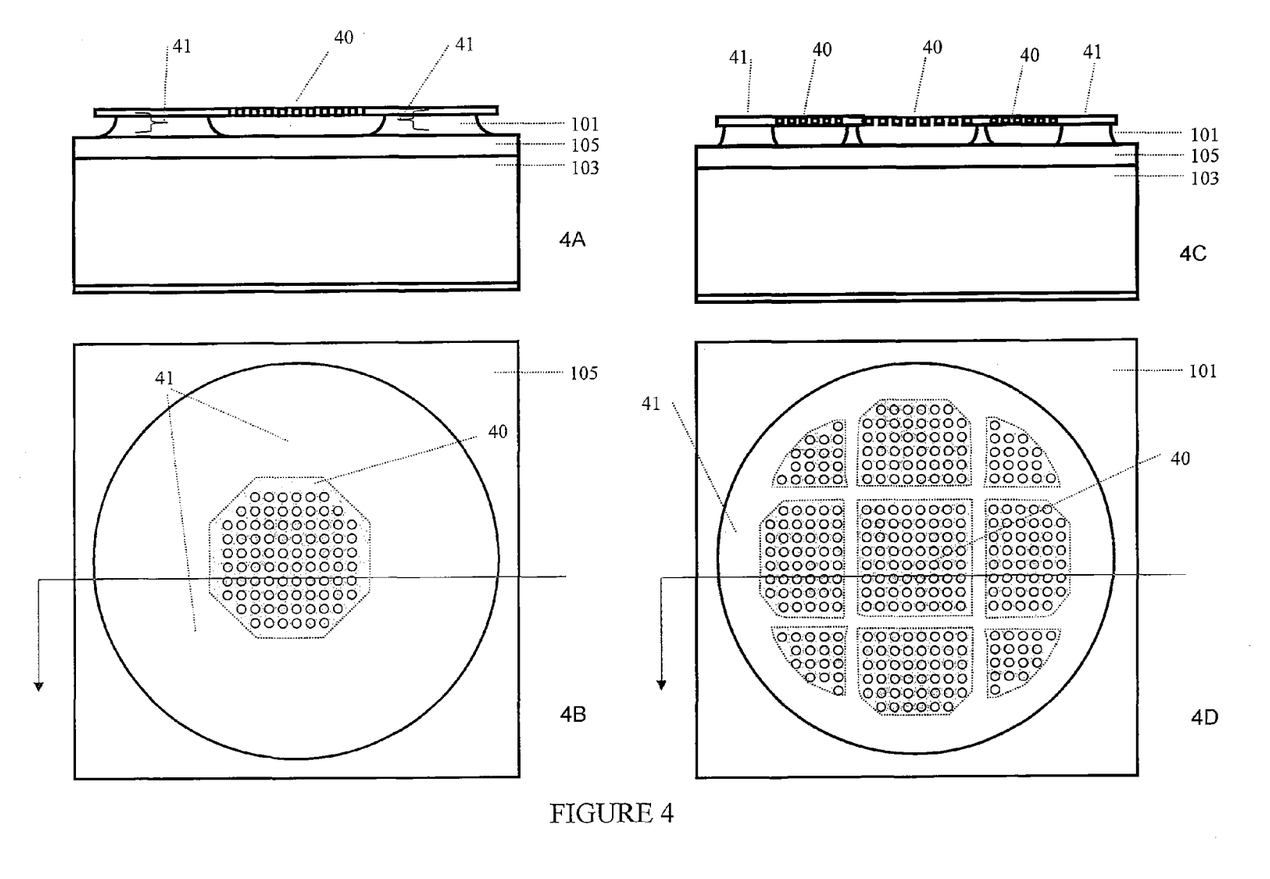
FIG. 4 illustrates the etched base layer 101.

The base layer 101 of the substrate 10 may be etched to achieve the dimensions desired for the base (see FIG. 4). In this step, etchant is applied in a manner which brings it into contact with the base layer via the holes in the etched sample support and along the perimeter of the sample support layer. This process serves to conform the shape of the base to the shape of the sample support. Etching is generally continued until the insulator 105 is exposed surrounding the perimeter of the etched sample support and surrounding the perimeter of the one or more holes and/or arrays of holes in the etched sample support. In areas with holes in the sample support layer 30, the underlying base layer 101 may be fully etched, resulting in a fully undercut, suspended sample support membrane 40. In the area without holes 31, the underlying base layer 101 is not fully etched, creating a frame region 41 comprised of the continuous sample support layer material 31 on the base layer 101. In areas external to frame region 41, including the sample support membrane area 40, the underlying insulator layer 105 is exposed.

In this step, an etching process is selected which is effective for etching the base layer but not for etching the insulator layer. A variety of etching processes may be used. Examples include wet etching, reactive ion etching (RIE), sputtering, ion milling, and deep reactive ion etching (DRIE). For the case of a silicon base layer, examples of etchants suitable for this step include: wet etch solution comprising 1:3:8 ratio of concentrated hydrofluoric acid, nitric acid, and acetic acid (HNA); $SF_6$-based silicon reactive ion etch; time-multiplexed $C_4F_8/SF_6$-based deep reactive ion; $XeF_2$-based silicon etch. In one embodiment, the base layer is etched using wet chemical etching, or reactive ion etching followed by a wet chemical etching, or deep reactive ion etching followed by a wet chemical etching.

Figure 5:
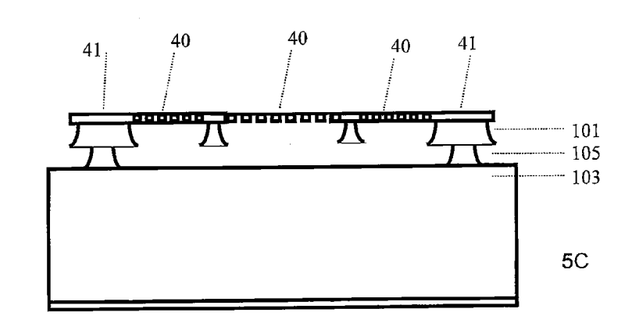
FIG. 5 illustrates insulator layer 105 etched using a wet chemical etch process.

The insulator layer may then be released, e.g., by physical means and/or by etching it away (see FIGS. 5 and 6). For example, the etching may be continued until all or substantially all of the insulator layer is removed thereby completely or substantially freeing the sample support structure.

The etching process is selected which is effective for etching the insulator layer but not for etching the sample support and insulator layers. A variety of etching processes, such as wet chemical etching, may be used in this step. For the case of a silicon dioxide insulator layer, examples of etchants suitable for this step include: concentrated hydrofluoric acid (HF) and buffered oxide etchant.

In a further embodiment, the final etching step of the insulator layer may be omitted. In yet a further embodiment, instead of a silicon-on-insulator substrate, a bulk silicon wafer may be used. In an aspect of this embodiment, the final etching step of the insulator layer may be omitted. In a further embodiment, other substrates, such as alumina, quartz, etc, may also be used.

The sample support structure may be useful in a variety of settings. Examples include electron and/or ion beam analysis, electron microscopy techniques, such as transmission electron microscopy. The sample support structures of the present invention have a number of improved properties, as compared to support structures of the art. For example, samples analyzed using the sample support structures of the present invention exhibit decreased drift, as compared to samples analyzed using sample support structures of the art. In addition, the presently described structures have increased rigidity; may in some embodiments lack the presence of grids, etc., which are required for structures of the art, and which result in lower quality imaging; and the sample support structures of the present invention may be used at various temperatures, ranging from very low to very high. Furthermore, the sample support structures of the present invention may have consistent thickness and low stress. The sample support structures of the present invention may provide the advantage of improved conductivity at very low temperatures, such as from about −270 to about 0° C.

In one embodiment, the sample support structure is used for conducting cryo transmission electron microscopy. The sample support structure can be brought into contact with a solution including a sample and rapidly frozen to preserve the ultrastructure of the sample. Sample may also be prepared by staining the sample with a heavy metal salt to enhance the signal-to-noise ratio, and freezing the sample on the sample support structure to preserve the high-resolution structure. The electron beam may be directed at the sample by transmitting the beam through the holes in the sample support.

The sample support of the invention is, in some embodiments, highly resistant to temperature changes. Consequently, in certain uses of the sample support structure, the sample support structure may be heated or cooled during processing.

The sample support structure may be useful for supporting samples containing a variety of components. In a particular non-limiting embodiment, various components that may be supported by the sample support structure include biological materials, whole cells, sections of cells, eukaryotic cells, prokaryotic cells, chemicals, proteins, peptides, polymers, nucleic acids, small molecules, and various combinations of these types of materials. In an embodiment, a protein sample may be supported by the sample support structure. In one embodiment, a protein and a compound, or a ligand, which interacts with the protein, may be supported by the sample support structure.

Further, the sample support structures may be useful in tomography studies, in which the sample support structure is tilted to obtain a series of images from different angles.

Non-limiting uses of the sample support structures include in: Transmission Electron Microscopy (TEM) Scanning Electron Microscopy (SEM), Scanning Transmission Electon Microscopy (STEM), and Scanning Tunneling Microscopy (STM). The use of the sample support structures in other applications known to one of skill in the art are contemplated herein.

Samples to be analyzed by the above techniques may be prepared in a number of ways, such as: cryofixation, fixation, dehydration, embedding, sectioning, staining, freeze-fracture or freeze-etch, ion beam milling, conductive coating, and/or, in scanning electron microscopy, evaporation, thin-film deposition, or sputtering of carbon, gold, gold/palladium, platinum or other conductive material to avoid charging of non conductive specimens in a scanning electron microscope.

It is hereby contemplated that sample analysis using the sample support structures combined with technologies described herein (such as electron microscopy), and/or other technologies known by one of skill in the art, may be used to obtain results similar to those obtained by X-ray crystallography techniques. However, these applications of the present invention have a number of advantages over X-ray crystallography, such as speed of sample preparation, etc.

The following non-limiting examples are provided only for the purpose of illustrating various aspects of the invention and should not be construed as limiting the scope of the invention.

Example 1

Referring to FIGS. 1, 2, 3A, 3B, 4A, 4B, 5A, 5B, 6A, and 6B, Silicon-on-insulator substrate 10, with monocrystalline base layer 101 with thickness 50 μm and a monocrystalline silicon substrate 103 with thickness 350 μm, separated by a silicon dioxide insulator layer 105 with thickness 1 μm, was provided. A silicon carbide sample support layer 20 with thickness 100 nm, was deposited using LPCVD.

The array 30, in FIGS. 3A and 3B, is comprised of individual holes with a 2 μm diameter on a 4 μm pitch. The array 30 was round with a diameter of 1 mm. The array 30 was fully surrounded by area without holes 31, and the distance from the perimeter of the array to the perimeter of the sample support was 1 mm. The diameter of the complete sample support device was 3 mm.

As further illustrated in FIGS. 3A and 3B, the silicon carbide sample support layer was etched using reactive ion etching with an $SF_6$-based etch recipe. As illustrated in FIGS. 4A and 4B, the base layer 101 was then etched using deep reactive ion etching down to the insulator layer 105. The deep reactive ion etch is extremely anisotropic and highly selective to silicon dioxide. The sample support was then etched using a solution comprised of hydrofluoric acid, nitric acid, and acetic acid, commonly known as HNA. HNA etches silicon isotropically, and the silicon present between holes features in the hole array 30 was fully etched.

As illustrated in FIGS. 5A and 5B, the silicon dioxide insulator layer 105 was etched using concentrated hydrofluoric acid. The sample substrate structure illustrated in FIGS. 6A and 6B was thus formed.

Example 2

Referring to FIGS. 1, 2, 3C, 3D, 4C, 4D, 5C, 5D, 6C, and 6D: Silicon-on-insulator substrate 10, with monocrystalline base layer 101 with thickness 50 μm and a monocrystalline silicon substrate 103 with thickness 350 μm, separated by a silicon dioxide insulator layer 105 with thickness 1 μm, was provided. A silicon carbide sample support layer 20 with thickness 100 nm, was deposited using LPCVD.

The array 30, in FIGS. 3C and 3D, is comprised of multiple arrays of individual holes with a 2 μm diameter on a 4 μm pitch. The array 30 was round with a diameter of 1 mm. The array 30 was fully surrounded by area without holes 31, and the distance from the perimeter of the array to the perimeter of the sample support was 1 mm. The diameter of the complete sample support device was 3 mm.

As further illustrated in FIGS. 3C and 3D, the silicon carbide sample support layer was etched using reactive ion etching with an $SF_6$ based etch recipe. As illustrated in FIGS. 4C and 4D, the base layer 101 was then etched using deep reactive ion etching down to the insulator layer 105. The portions of the base layer that were not beneath the arrays of holes were not fully etched. The deep reactive ion etch is extremely anisotropic and highly selective to silicon dioxide. The sample support was then etched using a solution comprised of hydrofluoric acid, nitric acid, and acetic acid, commonly known as HNA. HNA etches silicon isotropically, and the silicon present between holes features in the hole array 30 was fully etched. As above, the portions of the base layer that were not beneath the arrays of holes were not completely etched.

Figure 6A:
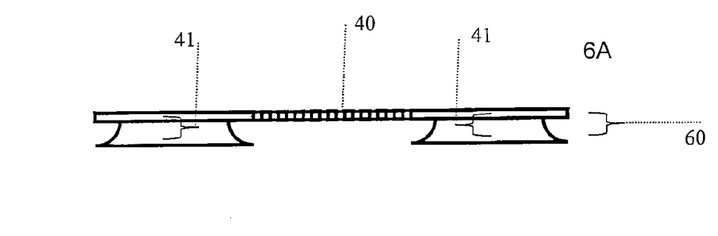
In FIGS. 6A and 6B, a sample support structure containing an array of holes is illustrated.
Figure 6B:
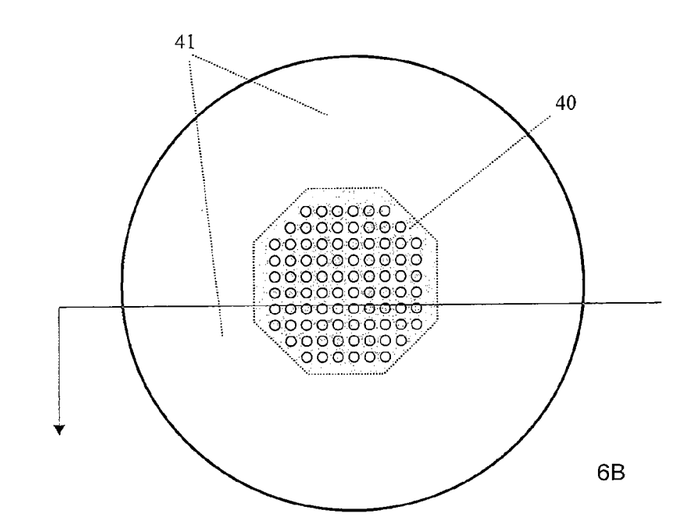
Figure 6C:
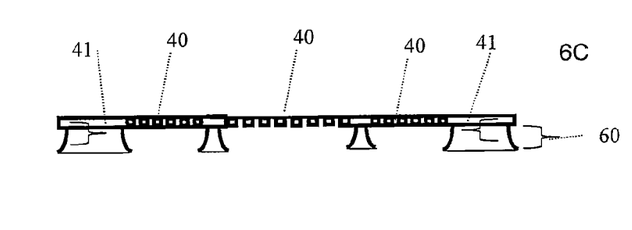
In FIGS. 6C and 6D, a sample support structure containing multiple arrays of holes is illustrated.
Figure 6D:
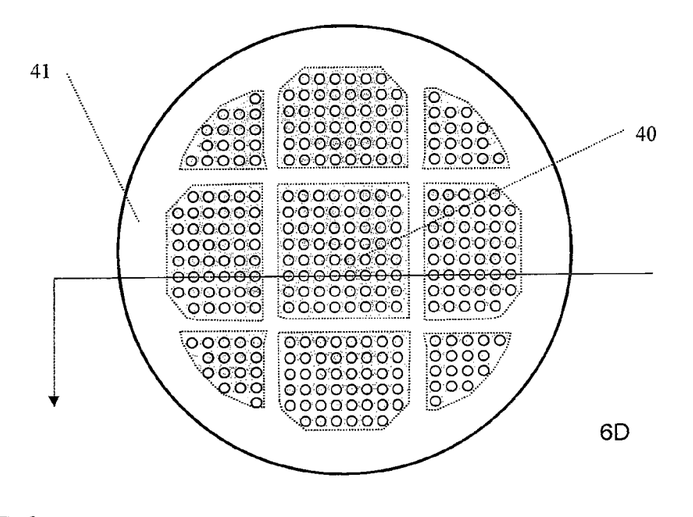

As illustrated in FIGS. 5C and 5D, the silicon dioxide insulator layer 105 was etched using concentrated hydrofluoric acid. The sample substrate structure as illustrated in FIGS. 6C and 6D was thus formed.

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art, based on the disclosure herein. The invention therefore is to be broadly construed, as encompassing all such variations, modifications and alternative embodiments within the spirit and scope of the claims hereafter set forth.

We claim:

1. A sample support structure comprising (i) a sample support comprising silicon carbide and having one or more holes therein, and (ii) a base underlying the sample support comprising an opening therein substantially surrounding the one or more holes of the sample support, wherein the thickness of the sample support is about 100 to 5000 Angstroms, and wherein the silicon carbide is doped to achieve a resistivity of less than about 10 ohm-cm.

2. The sample support structure of claim 1 wherein the sample support comprises at least one array of holes therein.

3. The sample support structure of claim 1 wherein the one or more holes in the sample support have a diameter ranging from about 0.5 to about 4 µm.

4. The sample support structure of claim 1 wherein the silicon carbide is doped with nitrogen.

5. The sample support structure of claim 1 wherein the base comprises a second material selected from the group consisting of monocrystalline silicon, polycrystalline silicon, amorphous silicon, alumina, quartz, fused silica, boron nitride, silicon carbide, metals, ceramics, and conducting oxides.

6. The sample support structure of claim 1 wherein the base:
   (a) has a shape which substantially tracks the perimeter of the sample support; and/or
   (b) comprises an opening therein, the perimeter of which substantially tracks the perimeter of the one or more array of holes in the sample support.

7. The sample support structure of claim 1 wherein:
   (a) the sample support comprises an array of holes therein; and
   (b) the base comprises a single opening substantially surrounding the array of holes.

8. A method of making a sample support structure, comprising the steps of:
   (a) providing a substrate comprising three layers:
      (i) a top base layer comprising an etchable base material;
      (ii) a middle insulator layer comprising an etchable insulator material; and
      (iii) a bottom substrate layer comprising an etchable substrate material;
   (b) applying a sample support layer comprising silicon carbide to the top base layer;
   (c) patterning dimensions of a sample support onto the sample support layer, wherein the dimensions include one or more holes;
   (d) etching the sample support layer to achieve dimensions established by the patterning step, including the one or more holes;
   (e) etching the base layer to achieve dimensions of a base;
   (f) etching the insulator layer to release or substantially release the insulator layer, thereby freeing or substantially freeing the bottom substrate layer from a sample support structure comprising:
      (i) a sample support comprising silicon carbide and having one or more holes therein; and
      (ii) a base underlying the sample support comprising an opening therein substantially surrounding the one or more holes of the sample support,
   wherein the thickness of the sample support is about 100 to 5000 Angstroms, and wherein the silicon carbide is doped to achieve a resistivity of less than about 10 ohm-cm.

9. The method of claim 8 wherein the silicon carbide is doped with nitrogen.

10. The method of claim 8 wherein the base layer comprises a material selected from a group consisting of monocrystalline silicon, polycrystalline silicon, amorphous silicon, alumina, quartz, fused silica, boron nitride, silicon carbide, metals, ceramics, and conducting oxides.

11. The method of claim 8 wherein the bottom substrate layer comprises a material selected from a group consisting of monocrystalline silicon, polycrystalline silicon, amorphous silicon, alumina, quartz, fused silica, boron nitride, silicon carbide, other semiconductor materials, metals, ceramics, and conducting oxide.

12. The method of claim 8 wherein the insulator layer comprises a material selected from a group consisting of silicon dioxide, fused silica, quartz, aluminum nitride, conducting oxides, and silicon monoxide.

13. The method of claim 8 wherein step (d) comprises etching the sample support layer using a technique selected from the group consisting of wet chemical etching, reactive ion etching (RIE), deep reactive ion etching (DRIE), and ion milling.

14. The method of claim 8 wherein step (c) comprises patterning at least one array of holes in a center portion of the sample support layer.

15. The method of claim 8, wherein the base layer is etched using wet chemical etching, or reactive ion etching followed by wet chemical etching, or deep reactive ion etching followed by wet chemical etching.

16. The method of claim 8, wherein the insulator layer is etched using wet chemical etching.

17. The method of claim 8 wherein the base layer of the substrate is etched using a deep reactive ion etching technique.

18. The method of claim 8 wherein step (e) comprises:
   (a) a first step comprising deep reactive ion etching; and
   (b) a second step comprising solution comprising hydrofluoric acid, nitric acid, and acetic acid (HNA).

19. The sample support structure of claim 1, wherein the thickness of the sample support is about 200 to about 1000 Angstroms.

20. The method of claim 8, wherein the base layer is etched via the one or more holes in the sample support layer.

* * * * *